United States Patent [19]

Oberdorf et al.

[11] Patent Number: 5,707,936
[45] Date of Patent: Jan. 13, 1998

[54] METHYL α-PHENYLBUTENOATES

[75] Inventors: Klaus Oberdorf; Hartmann König, both of Heidelberg; Bernd Müller, Frankenthal; Reinhard Kirstgen, Neustadt; Wassilios Grammenos, Ludwigshafen; Hubert Sauter, Mannheim; Gisela Lorenz, Hambach; Eberhard Ammermann, Heppenheim; Volker Harries, Frankenthal, all of Germany

[73] Assignee: BASF Aktiengesellschaft, Ludwigshafen, Germany

[21] Appl. No.: 732,300

[22] PCT Filed: Apr. 25, 1995

[86] PCT No.: PCT/EP95/01554

§ 371 Date: Oct. 31, 1996

§ 102(e) Date: Oct. 31, 1996

[87] PCT Pub. No.: WO95/29896

PCT Pub. Date: Nov. 9, 1995

[30] Foreign Application Priority Data

May 3, 1994 [DE] Germany .................. 44 15 483.6

[51] Int. Cl.⁶ .............. A01N 43/56; C07D 231/08; C07D 231/20; C07D 401/04; C07D 403/04
[52] U.S. Cl. .............. 504/253; 504/282; 514/341; 514/403; 514/407; 544/405; 546/276.1; 548/366.1; 548/366.4; 548/369.4; 548/371.1
[58] Field of Search .............. 504/253, 282; 514/341, 403, 407; 544/405; 546/276.1; 548/366.1, 366.4, 369.4, 371.1

[56] References Cited

U.S. PATENT DOCUMENTS

| | | |
|---|---|---|
| 4,937,372 | 6/1990 | Wenderoth et al. .......... 560/55 |
| 5,192,357 | 3/1993 | Cliff et al. .......... 504/282 X |
| 5,298,527 | 3/1994 | Grammenos et al. .......... 514/539 |

FOREIGN PATENT DOCUMENTS

| | | |
|---|---|---|
| 280 185 | 8/1988 | European Pat. Off. . |
| 513 580 | 11/1992 | European Pat. Off. . |

Primary Examiner—Fiona T. Powers
Attorney, Agent, or Firm—Keil & Weinkauf

[57] ABSTRACT

Methyl α-phenylbutenoates of the formula I

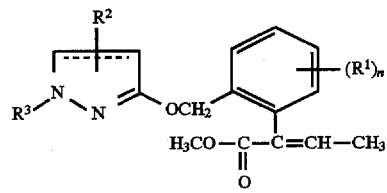

where -- is a single or double bond and the index and the substituents have the following meanings:

n is 0, 1, 2, 3 or 4;

$R^1$ is nitro, cyano, halogen, alkyl, haloalkyl or alkoxy;

$R^2$ is hydrogen, nitro, cyano, halogen, alkyl, haloalkyl, alkoxy, alkylthio or alkoxycarbonyl;

$R^3$ is unsubst. or subst. alkyl, alkenyl or alkynyl;

an unsubst. or subst. saturated or mono-or diunsaturated ring which, in addition to carbon atoms, can contain one to three of the following heteroatoms as ring members: oxygen, sulfur and nitrogen, or an unsubst. or subst. mono- or binuclear aromatic radical which, in addition to carbon atoms, can contain one to four nitrogen atoms or one or two nitrogen atoms and an oxygen or sulfur atom or an oxygen or sulfur atom as ring members, processes for their preparation and their use are described.

6 Claims, No Drawings

METHYL α-PHENYLBUTENOATES

This application is a 371 of PCT/EP95/01554 filed Apr. 25, 1995.

The present invention relates to methyl α-phenylbutenoates of the formula I

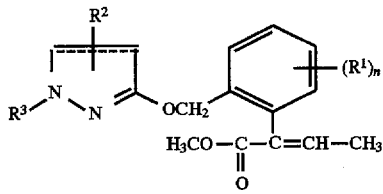

where ──── is a single or double bond and the index and the substituents have the following meanings:

n is 0, 1, 2, 3 or 4, it being possible for the substituents $R^1$ to be different if n is greater than 1;

$R^1$ is nitro, cyano, halogen, $C_1$–$C_4$-alkyl, $C_1$–$C_4$-haloalkyl or $C_1$–$C_4$-alkoxy;

$R^2$ is hydrogen, nitro, cyano, halogen, $C_1$–$C_4$-alkyl, $C_1$–$C_4$-haloalkyl, $C_1$–$C_4$-alkoxy, $C_1$–$C_4$-alkylthio or $C_1$–$C_4$-alkoxycarbonyl;

$R^3$ is unsubst. or subst. alkyl, alkenyl or alkynyl;

- an unsubst. or subst. saturated or mono-or diunsaturated ring which, in addition to carbon atoms, can contain one to three of the following heteroatoms as ring members: oxygen, sulfur and nitrogen, or
- an unsubst. or subst. mono-or binuclear aromatic radical which, in addition to carbon atoms, can contain one to four nitrogen atoms or one or two nitrogen atoms and an oxygen or sulfur atom or an oxygen or sulfur atom as ring members.

The invention additionally relates to processes for preparing these compounds, mixtures containing them and their use for controlling harmful fungi or animal pests.

EP-A 513 580 discloses methyl α-phenylbutenoates with action against harmful fungi or animal pests, which carry a 4-pyrazolyl-oxymethylene radical in the ortho position. The action of these compounds is unsatisfactory, however, at low application rates.

It is an object of the present invention to provide compounds having improved actions.

We have found that this is achieved by the compounds I defined at the outset. In addition, we have found processes for their preparation, mixtures containing them and methods for controlling harmful fungi and animal pests using the compounds I.

The compounds I can be obtained by various methods known per se from the literature.

For example, the compounds I are obtained by reaction of the benzyl derivative of the formula II with a 3-hydroxy (dihydro)-pyrazole of the formula III in the presence of a base.

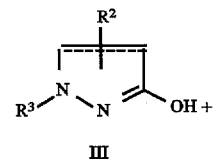

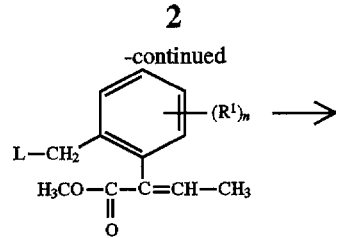

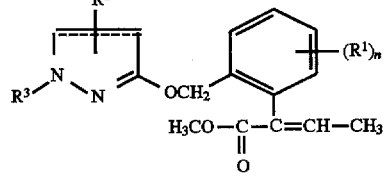

L in the formula II is a nucleophilically replaceable group, for example halogen, eg. chlorine, bromine or iodine, or an alkyl- or arylsulfonate, eg. methylsulfonate, trifluoromethylsulfonate, phenylsulfonate or 4-methylphenylsulfonate.

The reaction is customarily carried out at from 0° C. to 80° C., preferably from 20° C. to 60° C.

Suitable solvents are aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, i-propanol, n-butanol and tert-butanol, ketones such as acetone and methyl ethyl ketone, and also dimethyl sulfoxide, dimethylformamide, dimethylacetamide, 1,3-dimethylimidazolidin-2-one and 1,2-dimethyltetrahydro-2(1H)-pyrimidine, preferably methylene chloride, acetone and dimethylformamide. Mixtures of the solvents mentioned can also be used.

Suitable bases are generally inorganic compounds such as alkali metal and alkaline earth metal hydroxides (eg. lithium hydroxide, sodium hydroxide, potassium hydroxide and calcium hydroxide), alkali metal and alkaline earth metal oxides (eg. lithium oxide, sodium oxide, calcium oxide and magnesium oxide), alkali metal and alkaline earth metal hydrides (eg. lithium hydride, sodium hydride, potassium hydride and calcium hydride), alkali metal amides (eg. lithium amide, sodium amide and potassium amide), alkali metal and alkaline earth metal carbonates (eg. lithium carbonate and calcium carbonate) and also alkali metal hydrogen carbonates (eg. sodium hydrogen carbonate), organometallic compounds, in particular alkali metal alkyls (eg. such as methyllithium, butyllithium and phenyllithium), alkylmagnesium halides (eg. methylmagnesiumchloride) and also alkali metal and alkaline earth metal alkoxides (eg. sodium methoxide, sodium ethoxide, potassium ethoxide, potassium tert-butoxide and dimethoxymagnesium), additionally organic bases, eg. tertiary amines such as trimethylamine, triethylamine, triisopropylethylamine and N-methylpiperidine, pyridine, substituted pyridines such as collidine, lutidine and 4-dimethylaminopyridine and also bicyclic amines.

Sodium hydroxide, potassium carbonate and potassium tert-butoxide are particularly preferred.

The bases are in general used in equimolar amounts, in an excess or, if appropriate, as a solvent.

It may be advantageous for the reaction to add a catalytic amount of a crown ether (eg. 18-crown-6 or 15-crown-5).

The reaction can also be carried out in two-phase systems consisting of a solution of alkali metal or alkaline earth metal hydroxides or carbonates in water and an organic phase (eg. aromatic and/or halogenated hydrocarbons). Suitable phase-transfer catalysts in this case are, for example, ammonium halides and tetrafluoroborates (eg. benzyltriethylammonium chloride, benzyltributylammonium bromide, tetrabutylammonium chloride, hexadecyltrimethylammoniumbromide or tetrabutylammonium tetrafluoroborate) and also phosphonium halides (eg. tetrabutylphosphonium chloride and tetraphenylphosphonium bromide).

It may be advantageous for the reaction first to convert the 3-hydroxy(dihydro)pyrazole with the base to the corresponding hydroxylate, which is then reacted with the benzyl derivative.

The starting substances II required for the preparation of the compounds I are disclosed in EP-A 513 580. Compounds II in which L is chlorine or bromine are accordingly obtained by reaction of appropriate ethers (alkyl or aryl ethers) with halogenating agents [Hal] (eg. boron trichloride, hydrogen bromide) in an inert solvent (eg. halogensted and/or aromatic hydrocarbons) at from −30° C. to 40° C.

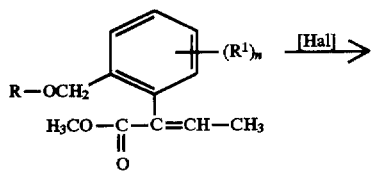

(R = alkyl, aryl)

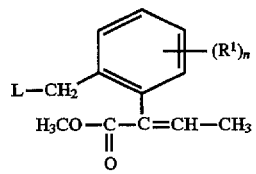

II (L = halogen)

3-Hydroxypyrazoles IIIa and 3-hydroxydihydropyrazoles IIIb (or their tautomeric form: 3-pyrazolones) are known from the literature or can be prepared by the methods described there [IIIa: J. Heterocycl. Chem. 30 (1993), 49; Chem. Ber. 107 (1974), 1318; Chem. Pharm. Bull. 19 (1971), 1389; Tetrahedron Lett. 11 (1970), 875; Chem. Heterocycl. Comp. 5 (1969), 527; Chem. Ber. 102 (1969), 3260; Chem. Ber. 109 (1976), 261; J. Org. Chem. 31 (1966), 1538; Tetrahedron 43 (1987), 607; IIIb: J. Med. Chem. 19 (1976), 715].

The compounds I are obtained in a similar manner to the methods described in EP-A 513 580 by the processes compiled in the following reaction scheme (with respect to the process parameters reference may be made to the details in EP-A 513 580, whose disclosure is hereby included with respect to the preparation process).

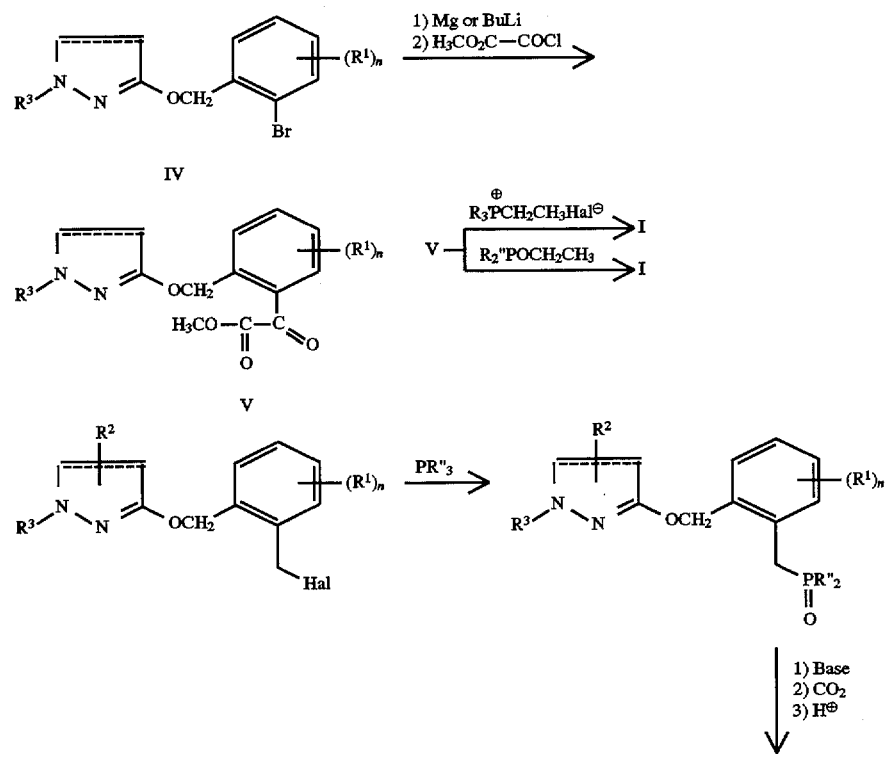

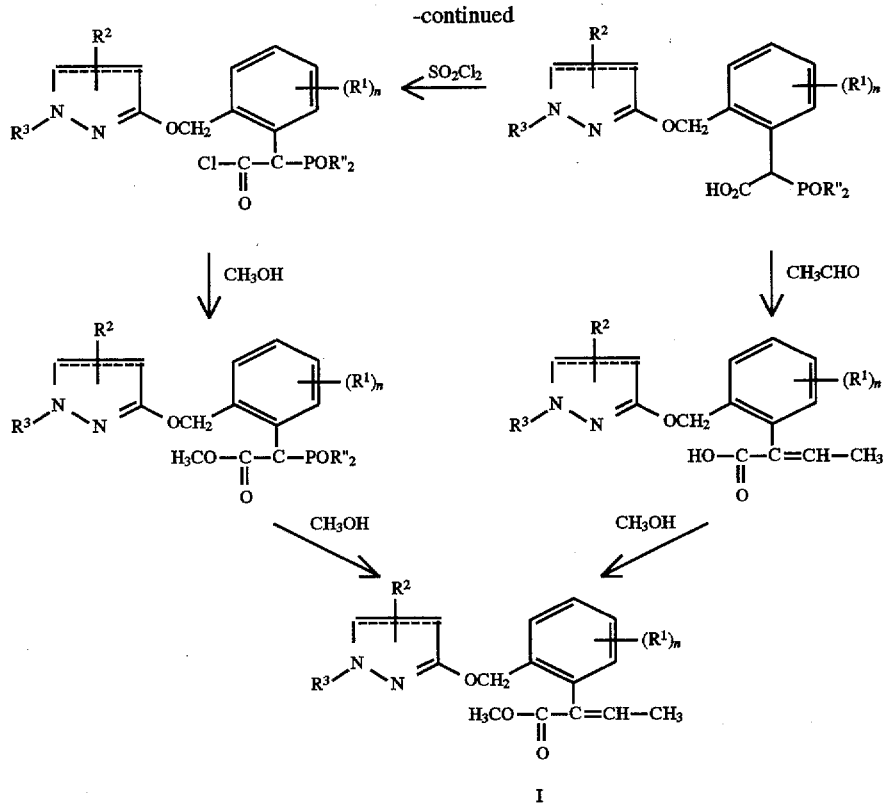

With respect to the butenoic acid double bond, the compounds I can exist both as E- and Z-isomers. Both isomers can be used separately or together in the manner according to the invention. Mixtures of the isomers are preferred, in particular the E isomer (configuration with respect to the carboxylate methyl position).

In the definitions of the symbols given in the above formulae, collective terms were used which are generally representative of the following substituents:

halogen: fluorine, chlorine, bromine and iodine;

alkyl: saturated, straight-chain or branched hydrocarbon radicals having 1 to 4 carbon atoms, eg. methyl, ethyl, propyl, 1-methylethyl, butyl, 1-methylpropyl, 2-methylpropyl and 1,1-dimethylethyl;

haloalkyl: straight-chain or branched alkyl groups having 1 to 4 carbon atoms (as mentioned above), it being possible for the hydrogen atoms these in [sic] groups to be partly or completely replaced by halogen atoms as mentioned above, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups having 1 to 4 carbon atoms (as mentioned above), which are bonded to the structure via an oxygen atom (—O—);

alkoxycarbonyl: straight-chain or branched alkoxy groups having 1 to 4 carbon atoms (as mentioned above), which are bonded to the structure via a carbonyl group (—CO—);

alkylthio: straight-chain or branched alkyl groups having 1 to 4 carbon atoms (as mentioned above), which are bonded to the structure via a sulfur atom (—S—);

unsubst. or subst. alkyl: saturated, straight-chain or branched hydrocarbon radicals, in particular having 1 to 10 carbon atoms, eg. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-di-methylbutyl, 2,3-dimethylbutyl, 3,3-dimethytbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

unsubst. or subst. alkenyl: unsaturated, straight-chain or branched hydrocarbon radicals, in particular having 2 to 10 carbon atoms and a double bond in any desired position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl- 1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched hydrocarbon groups, in particular having 2 to 20 carbon atoms and a triple bond in any desired position, eg. $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

an unsubst. or subst. saturated or mono-or diunsaturated ring which, in addition to carbon atoms, can contain one to three of the following heteroatoms as ring members: oxygen, sulfur and nitrogen, for example carbocycles such as cyclopropyl, cyclopentyl, cyclohexyl, cyclopent-2-enyl, cyclohex-2-enyl, 5- to 6-membered, saturated or unsaturated heterocycles, containing one to three nitrogen atoms and/or an oxygen or sulfur atom, such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidinyl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl and 1,2,4-tetrahydrotriazin-3-yl, preferably 2-tetrahydrofuranyl, 2-tetrahydrothienyl, 2-pyrrolidinyl, 3-isoxazolidinyl, 3-isothiazolidinyl, 1,3,4-oxazolidin-2-yl, 2,3-dihydrothien-2-yl, 4,5-isoxazolin-3-yl, 3-piperidinyl, 1,3-dioxan-5-yl, 4-piperidinyl, 2-tetrahydropyranyl, 4-tetrahydropyranyl;

or an unsubst. or subst. mono-or binuclear aromatic ring system which, in addition to carbon atoms, can contain one to four nitrogen atoms or one or two nitrogen atoms and an oxygen or sulfur atom or an oxygen or sulfur atom as ring members, ie. aryl radicals such as phenyl and naphthyl, preferably phenyl or 1- or 2-naphthyl, and hetaryl radicals, for example 5-membered ring heteroaromatics containing one to three nitrogen atoms and/or an oxygen or sulfur atom, such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,5-triazol-3-yl, 1,2,3-triazol-4-yl, 1,2,3-triazol-5-yl, 1,2,3-triazol-4-yl, 5-tetrazolyl, 1,2,3,4-thiatriazol-5-yl and 1,2,3,4-oxatriazol-5-yl, in particular 3-isoxazolyl, 5-isoxazolyl, 4-oxazolyl, 4-thiazolyl, 1,3,4-oxadiazol-2-yl and 1,3,4-thiadiazol-2-yl or, for example, 6-membered ring heteroaromatics containing one to four nitrogen atoms as heteroatoms, such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl, in particular 2-pyridinyl, 3-pyridinyl, 4-pyridinyl, 2-pyrimidinyl, 4-pyrimidinyl, 2-pyrazinyl and 4-pyridazinyl.

The addition of unsubst. or subst. with respect to alkyl, alkenyl and alkynyl groups is intended to express that these groups can be partly or completely halogenated (ie. the hydrogen atoms of these groups can can [sic] be partly or completely replaced by identical or different halogen atoms such as mentioned above, preferably fluorine, chlorine and bromine, in particular fluorine and chlorine) and/or can carry one to three, in particular one, of the following radicals:

cyano, nitro, $C_1$–$C_4$-alkoxy, $C_1$–$C_4$-halalkoxy [sic], $C_1$–$C_4$-alkylthio or an unsubst. or subst. mono-or binuclear aromatic ring system which, in addition to carbon atoms, can contain one to four nitrogen atoms or one or two nitrogen atoms and an oxygen or sulfur atom or an oxygen or sulfur atom as ring members, ie. aryl radicals such as phenyl and naphthyl, preferably phenyl or 1- or 2-naphthyl, and hetaryl radicals, for example 5-membered ring heteroaromatics containing one to three nitrogen atoms and/or an oxygen or sulfur atom, such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,5-triazol-3-yl, 1,2,3-triazol-4-yl, 1,2,3-triazol-5-yl, 1,2,3-triazol-4-yl, 5-tetrazolyl, 1,2,3,4-thiatriazol-5-yl and 1,2,3,4-oxatriazol-5-yl, in particular 3-isoxazolyl, 5-isoxazolyl, 4-oxazolyl, 4-thiazolyl, 1,3,4-oxadiazol-2-yl and 1,3,4-thiadiazol-2-yl or, for example, 6-membered ring heteroaromatics containing one to four nitrogen atoms as heteroatoms, such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4, 5-tetrazin-3-yl, in particular 2-pyridinyl, 3-pyridinyl, 4-pyridinyl, 2-pyrimidinyl, 4-pyrimidinyl, 2-pyrazinyl and 4-pyridazinyl.

The addition of unsubst. or subst. with respect to the cyclic (saturated, unsaturated or aromatic) groups is intended to express that these groups can be partly or completely halogenated (ie. the hydrogen atoms of these groups can can [sic] be partly or completely replaced by identical or different halogen atoms such as mentioned above, preferably fluorine, chlorine and bromine, in particular fluorine and chlorine) and/or can carry one to three of the following radicals: nitro, cyano, $C_1$–$C_4$-alkyl or $C_1$–$C_4$-alkoxy.

The mono-or binuclear aromatic or heteroaromatic systems mentioned under the radicals can in turn be partly or completely halogenated, ie. the hydrogen atoms of these groups can be partly or completely replaced by halogen atoms such as fluorine, chlorine, bromine and iodine, preferably fluorine and chlorine.

In addition to the halogen atoms designated, these mono- or binuclear aromatic or heteroaromatic systems can additionally carry one to three of the following substituents:

nitro;

cyano, thiocyanato;

alkyl, particularly $C_1$–$C_6$-alkyl as mentioned above, preferably methyl, ethyl, 1-methylethyl, 1,1-dimethylethyl, butyl, hexyl, in particular methyl and 1-methylethyl;

$C_1$–$C_4$-haloalkyl, as mentioned above, preferably trichloromethyl, difluoromethyl, trifluoromethyl, 2,2-difluoroethyl, 2,2,2-trifluoroethyl and pentafluoroethyl;

$C_1$–$C_4$-alkoxy, preferably methoxy, ethoxy, 1-methylethoxy and 1,1-dimethylethoxy, in particular methoxy;

$C_1$–$C_4$-haloalkoxy, particularly $C_1$–$C_2$-haloalkoxy, preferably difluoromethoxy, trifluoromethoxy and 2,2,2-trifluoroethoxy, in particular difluoromethoxy;

$C_1$–$C_4$-alkylthio, preferably methylthio and 1-methylethylthio, in particular methylthio;

$C_1$–$C_4$-alkylamino such as methylamino, ethylamino, propylamino, 1-methylethylamino, butylamino, 1-methylpropylamino, 2-methylpropylamino and 1,1-dimethylethylamino, preferably methylamino and 1,1-dimethylethylamino, in particular methylamino, di-$C_1$–$C_4$-alkyiamino such as N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)-amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino, preferably N,N-dimethylamino and N,N-diethylamino, in particular N,N-dimethylamino;

$C_1$–$C_6$-alkylcarbonyl such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl and 1-ethyl-2-methylpropylcarbonyl, preferably methylcarbonyl, ethylcarbonyl and 1,1-dimethylcarbonyl, in particular ethylcarbonyl;

$C_1$–$C_6$-alkoxycarbonyl such as methoxycarbonyl, ethoxycarbonyl, propoxycarbonyl, 1-methylethoxycarbonyl, butoxycarbonyl, 1-methylpropoxycarbonyl, 2-methylpropoxycarbonyl, 1,1-dimethylethoxycarbonyl, pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexyloxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl and 1-ethyl-2-methylpropoxycarbonyl, preferably methoxycarbonyl, ethoxycarbonyl and 1,1-dimethylethoxycarbonyl, in particular ethoxycarbonyl;

$C_1$–$C_6$-alkylaminocarbonyl such as methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl, 1,1-dimethylethylaminocarbonyl, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl and 1-ethyl-2-methylpropylaminocarbonyl, preferably methylaminecarbonyl [sic] and ethylaminecarbonyl [sic], in particular methylaminocarbonyl;

di-$C_1$-$C_6$-alkylaminocarbonyl, particularly di-$C_1$-$C_4$-alkylaminocarbonyl such as N,N-dimethylaminocarbonyl, N,N-diethylaminocarbonyl, N,N-dipropylaminocarbonyl, N,N-di(1-methylethyl)aminocarbonyl, N,N-dibutylaminocarbonyl, N,N-di(1-methylpropyl)aminocarbonyl, N,N-di(2-methylpropyl)aminocarbonyl, N,N-di(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-di-methylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methyl-propyl)aminocarbonyl, N-(1,1-dimethylethyl)-N-(1-methylpropyl)aminocarbonyl and N-(1,1-dimethylethyl)-N-(2-methylpropyl)aminocarbonyl, preferably N,N-dimethylaminocarbonyl and N,N-diethylaminecarbonyl [sic], in particular N,N-dimethylaminocarbonyl;

$C_1$-$C_6$-alkylcarboxyl such as methylcarboxyl, ethylcarboxyl, propylcarboxyl, 1-methylethylcarboxyl, butylcarboxyl, 1-methylpropylcarboxyl, 2-methylpropylcarboxyl, 1,1-dimethylethylcarboxyl, pentylcarboxyl, 1-methylbutylcarboxyl, 2-methylbutylcarboxyl, 3-methylbutylcarboxyl, 1,1-dimethylpropylcarboxyl, 1,2-dimethylpropylcarboxyl, 2,2-dimethylpropylcarboxyl, 1-ethylpropylcarboxyl, hexylcarboxyl, 1-methylpentylcarboxyl, 2-methylpentylcarboxyl, 3-methylpentylcarboxyl, 4-methylpentylcarboxyl, 1,1-dimethylbutylcarboxyl, 1,2-dimethylbutylcarboxyl, 1,3-dimethylbutylcarboxyl, 2,2-dimethylbutylcarboxyl, 2,3-dimethylbutylcarboxyl, 3,3-dimethylbutylcarboxyl, 1-ethylbutylcarboxyl, 2-ethylbutylcarboxyl, 1,1,2-trimethylpropylcarboxyl, 1,2,2-trimethylpropylcarboxyl, 1-ethyl-1-methylpropylcarboxyl and 1-ethyl-2-methylpropylcarboxyl, preferably methylcarboxyl, ethylcarboxyl and 1,1-dimethylethylcarbonyl, in particular methylcarboxyl and 1,1-dimethylethylcarboxyl;

$C_1$-$C_6$-alkylcarbonylamino such as methylcarbonylamino, ethylcarbonylamino, propylcarbonylamino, 1-methylethylcarbonylamino, butylcarbonylamino, 1-methylpropylcarbonylamino, 2-methylpropylcarbonylamino, 1,1-dimethylethylcarbonylamino, pentylcarbonylamino, 1-methylbutylcarbonylamino, 2-methylbutylcarbonylamino, 3-methylbutylcarbonylamino, 2,2-dimethylpropylcarbonylamino, 1-ethylpropylcarbonylamino, hexylcarbonylamino, 1,1-dimethylpropylcarbonylamino, 1,2-dimethylpropylcarbonylamino, 1-methylpentylcarbonylamino, 2-methylpentylcarbonylamino, 3-methylpentylcarbonylamino, 4-methylpentylcarbonylamino, 1,1-dimethylbutylcarbonylamino, 1,2-dimethylbutylcarbonylamino, 1,3-dimethylbutylcarbonylamino, 2,2-dimethylbutylcarbonylamino, 2,3-dimethylbutylcarbonylamino, 3,3-dimethylbutylcarbonylamino, 1-ethylbutylcarbonylamino, 2-ethylbutylcarbonylamino, 1,1,2-trimethylpropylcarbonylamino, 1,2,2-trimethylpropylcarbonylamino, 1-ethyl-1-methylpropylcarbonylamino and 1-ethyl-2-methylpropylcarbonylamino, preferably methylcarbonylamino and ethylcarbonylamino, in particular ethylcarbonylamino;

$C_3$-$C_7$-cycloalkyl such as cyclopropyl, cyclobutyl, cyclopentyl, cyclohexyl and cycloheptyl, preferably cyclopropyl, cyclopentyl and cyclohexyl, in particular cyclopropyl;

$C_3$-$C_7$-cycloalkoxy such as cyclopropoxy, cyclobutoxy, cyclopentoxy, cyclohexyloxy and cycloheptyloxy, preferably cyclopentoxy and cyclohexyloxy, in particular cyclohexyloxy;

$C_3$-$C_7$-cycloalkylthio such as cyclopropylthio, cyclobutylthio, cyclopentylthio, cyclohexylthio and cycloheptylthio, preferably cyclohexylthio;

$C_3$-$C_7$-cycloalkylamino such as cyclopropylamino, cyclobutylamino, cyclopentylamino, cyclohexylamino and cycloheptylamino, preferably cyclopropylamino and cyclohexylamino, in particular cyclopropylamino;

Two adjacent radicals on $R^3$ can have the meaning of an oxy-$C_1$-$C_2$-alkylidenoxy chain which is unsubstituted or substituted by fluorine, such as eg. —O—$CH_2$—O—, —O—$CF_2$—O—, —O—$CH_2CH_2$—O— or —O—$CF_2CF_2$—O—, or a $C_3$-$C_4$-alkylidene chain, such as eg. propylidene or butylidene.

With respect to their biological action, compounds I are preferred in which n is 0 or 1.

Equally, compounds I are preferred in which $R^1$ is halogen, $C_1$-$C_4$-alkyl, $C_1$-$C_2$-haloalkyl or $C_1$-$C_2$-alkoxy.

Additionally, compounds I are preferred in which $R^2$ is hydrogen, nitro, halogen, $C_1$-$C_4$-alkyl, $C_1$-$C_2$-haloalkyl or $C_1$-$C_2$-alkoxycarbonyl.

In addition, compounds I are preferred in which $R^3$ is unsubst. or subst. $C_1$-$C_4$-alkyl or $C_3$-$C_6$-cycloalkyl.

Equally, compounds I are preferred in which $R^3$ is an unsubst. or subst. saturated or mono-or diunsaturated ring which, in addition to carbon atoms, can contain one to three of the following heteroatoms as ring members: oxygen, sulfur and nitrogen.

Additionally, compounds I are preferred in which $R^3$ is an unsubst. or subst. mono-or binuclear aromatic radical which, in addition to carbon atoms, can contain one to four nitrogen atoms or one or two nitrogen atoms and an oxygen or sulfur atom or an oxygen or sulfur atom as ring members.

In addition, compounds I are preferred in which $R^3$ is an unsubst. or subst. 5-membered ring heteroaromatic.

In addition, compounds I are preferred in which $R^3$ is an unsubst. or subst. 6-membered ring heteroaromatic.

In particular, compounds I are preferred in which $R^1$ is hydrogen (n=0), chlorine, methyl or trifluoromethyl.

In particular, compounds I are additionally preferred in which $R^2$ is hydrogen, halogen, methyl, trifluoromethyl or methoxycarbonyl.

Equally, compounds I are in particular preferred in which $R^3$ is $C_1$-$C_4$-alkyl.

Additionally, compounds I are in particular preferred in which $R^3$ is $C_3$-$C_6$-cycloalkyl which can carry one to three $C_1$-$C_4$-alkyl groups.

In particular, compounds I are in addition preferred in which $R^3$ is unsubst. or subst. phenyl.

In particular, compounds I are also preferred in which $R^3$ is unsubst. or subst. pyridyl or pyrimidyl.

In particular, those compounds I are preferred in which $R^3$ is unsubstituted or substituted phenyl or benzyl. Suitable substituents of the phenyl radical in these cases are preferably halogen, cyano, $C_1$-$C_4$-alkyl, $C_1$-$C_4$-alkoxy, $C_1$-$C_2$-haloalkyl, $C_1$-$C_2$-haloalkoxy, phenyl and oxy-$C_1$-$C_2$-alkylidenoxy.

Also preferred are those compounds I in which $R^3$ is unsubstituted or substituted five-membered ring heteroaromatics such as eg. thiazolyl, isoxazolyl or oxazolyl. Suitable substituents of the five-membered ring heteroaromatics are preferably halogen, cyano, $C_1$-$C_6$-alkyl, $C_1$-$C_6$-alkoxy, $C_1$-$C_4$-haloalkyl, $C_1$-$C_2$-haloalkoxy and phenyl.

Also preferred are those compounds I in which $R^3$ is unsubstituted or substituted six-membered ring heteroaromatics, such as eg. pyridyl, pyrimidyl, pyridazinyl or pyrazinyl. Suitable substituents of the six-membered ring heteroaromatics are preferably halogen, cyano, $C_1$-$C_4$-alkyl, $C_1$-$C_4$-alkoxy, $C_1$-$C_2$-haloalkyl, $C_1$-$C_2$-haloalkoxy and phenyl.

Examples of particularly preferred compounds I are compiled in the following tables.

Table 1

Compounds of the general formula I.1 in which $R^2$ is hydrogen and the combination of the substituents $R_n^1$ and $R^3$ for one compound in each case corresponds to one line of Table A.

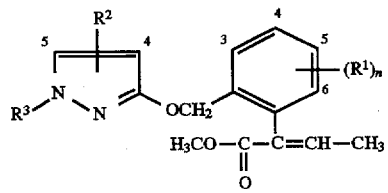

Table 2

Compounds of the general formula I.2 in which $R^2$ is hydrogen and the combination of the substituents $R_n^1$ and $R^3$ for one compound in each case corresponds to one line of Table A.

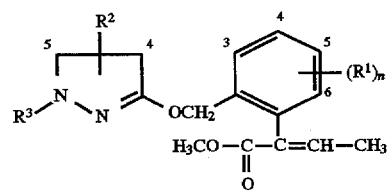

Table 3

Compounds of the general formula I.1 in which $R^2$ is 4-Cl and the combination of the substituents $R_n^1$ and $R^3$ for one compound in each case corresponds to one line of Table A.

Table 4

Compounds of the general formula I.1 in which $R^2$ is 4-Br and the combination of the substituents $R_n^1$ and $R^3$ for one compound in each case corresponds to one line of Table A.

Table 5

Compounds of the general formula I.1, in which $R^2$ is 5-$CH_3$ and the combination of the substituents $R_n^1$ and $R^3$ for one compound in each case corresponds to one line of Table A.

Table 6

Compounds of the general formula I.1, in which $R^2$ is 5-$CF_3$ and the combination of the substituents $R_n^1$ and $R^3$ for one compound in each case corresponds to one line of Table A.

Table 7

Compounds of the general formula I.1, in which $R^2$ is 4-$CO_2CH_3$ and the combination of the substituents $R_n^1$ and $R^3$ for one compound in each case corresponds to one line of Table A.

TABLE A

| $R_n^1$ | $R^3$ |
|---|---|
| H | $C_6H_5$ |
| 3-Cl | $C_6H_5$ |
| 4-Cl | $C_6H_5$ |
| 6-Cl | $C_6H_5$ |
| 4-F | $C_6H_5$ |
| 4-$OCH_3$ | $C_6H_5$ |
| 3-$CH_3$ | $C_6H_5$ |
| 6-$CH_3$ | $C_6H_5$ |
| H | 2-F—$C_6H_4$ |
| H | 3-F—$C_6H_4$ |
| H | 4-F—$C_6H_4$ |
| H | 2,3-$F_2$—$C_6H_3$ |
| H | 2,4-$F_2$—$C_6H_3$ |
| H | 2,5-$F_2$—$C_6H_3$ |
| H | 2,6-$F_2$—$C_6H_3$ |
| H | 3,4-$F_2$—$C_6H_3$ |
| H | 3,5-$F_2$—$C_6H_3$ |
| H | 2-Cl—$C_6H_4$ |
| H | 3-Cl—$C_6H_4$ |
| H | 4-Cl—$C_6H_4$ |
| 3-Cl | 4-Cl—$C_6H_4$ |
| 4-Cl | 4-Cl—$C_6H_4$ |
| 6-Cl | 4-Cl—$C_6H_4$ |
| 4-F | 4-Cl—$C_6H_4$ |
| 4-$OCH_3$ | 4-Cl—$C_6H_4$ |
| 3-$CH_3$ | 4-Cl—$C_6H_4$ |
| 6-$CH_3$ | 4-Cl—$C_6H_4$ |
| H | 2,3-$Cl_2$—$C_6H_3$ |
| H | 2,4-$Cl_2$—$C_6H_3$ |
| H | 2,5-$Cl_2$—$C_6H_3$ |
| H | 2,6-$Cl_2$—$C_6H_3$ |
| H | 3,4-$Cl_2$—$C_6H_3$ |
| H | 3,5-$Cl_2$—$C_6H_3$ |
| H | 2,3,4-$Cl_3$—$C_6H_2$ |
| H | 2,3,5-$Cl_3$—$C_6H_2$ |
| H | 2,3,6-$Cl_3$—$C_6H_2$ |
| H | 2,4,5-$Cl_3$—$C_6H_2$ |
| H | 2,4,6-$Cl_3$—$C_6H_2$ |
| H | 3,4,5-$Cl_3$—$C_6H_2$ |
| H | 2-Br—$C_6H_4$ |
| H | 3-Br—$C_6H_4$ |
| H | 4-Br—$C_6H_4$ |
| H | 2,4-$Br_2$—$C_6H_3$ |
| H | 2-Br, 4-F—$C_6H_3$ |
| H | 2-Br, 4-Cl—$C_6H_3$ |
| H | 2-F, 4-Cl—$C_6H_3$ |
| H | 3-F, 4-Cl—$C_6H_3$ |
| H | 3-Cl, 5-F—$C_6H_3$ |
| H | 2-Cl, 4-F—$C_6H_3$ |
| H | 2-CN—$C_6H_4$ |
| H | 3-CN—$C_6H_4$ |
| H | 4-CN—$C_6H_4$ |
| H | 3-CN, 4-Cl—$C_6H_3$ |

TABLE A-continued

| $R^1_n$ | $R^3$ |
|---|---|
| H | 4-NO$_2$—C$_6$H$_4$ |
| H | 2-CH$_3$—C$_6$H$_4$ |
| H | 3-CH$_3$—C$_6$H$_4$ |
| H | 4-CH$_3$—C$_6$H$_4$ |
| H | 2,4-(CH$_3$)$_2$—C$_6$H$_3$ |
| H | 2,5-(CH$_3$)$_2$—C$_6$H$_3$ |
| H | 2,5-(CH$_3$)$_2$—C$_6$H$_3$ |
| H | 2,6-(CH$_3$)$_2$—C$_6$H$_3$ |
| H | 3,4-(CH$_3$)$_2$—C$_6$H$_3$ |
| H | 3,5-(CH$_3$)$_2$—C$_6$H$_3$ |
| H | 2,4,6-(CH$_3$)$_3$—C$_6$H$_2$ |
| H | 3,4,5-(CH$_3$)$_3$—C$_6$H$_2$ |
| H | 2-CH$_3$, 4-Cl—C$_6$H$_3$ |
| H | 2-Cl, 4-CH$_3$—C$_6$H$_3$ |
| H | 3-CH$_3$, 4-Cl—C$_6$H$_3$ |
| H | 3-Cl, 5-CH$_3$—C$_6$H$_3$ |
| H | 2-CN, 4-CH$_3$—C$_6$H$_3$ |
| H | 2-CH$_3$, 4-CN—C$_6$H$_3$ |
| H | 4-(C$_2$H$_5$)—C$_6$H$_4$ |
| H | 4-[C(CH$_3$)$_3$]—C$_6$H$_4$ |
| H | 3-(C$_6$H$_5$)—C$_6$H$_4$ |
| H | 4-(C$_6$H$_5$)—C$_6$H$_4$ |
| H | 2-CF$_3$—C$_6$H$_4$ |
| H | 3-CF$_3$—C$_6$H$_4$ |
| H | 4-CF$_3$—C$_6$H$_4$ |
| H | 3,5-(CF$_3$)$_2$—C$_6$H$_3$ |
| H | 2-Cl, 4-CF$_3$—C$_6$H$_3$ |
| H | 2-OCH$_3$—C$_6$H$_4$ |
| H | 3-OCH$_3$—C$_6$H$_4$ |
| H | 4-OCH$_3$—C$_6$H$_4$ |
| H | 2,4-(OCH$_3$)$_2$—C$_6$H$_3$ |
| H | 3,4-(OCH$_3$)$_2$—C$_6$H$_3$ |
| H | 2,5-(OCH$_3$)$_2$—C$_6$H$_3$ |
| H | 3,5-(OCH$_3$)$_2$—C$_6$H$_3$ |
| H | 3,4,5-(OCH$_3$)$_3$—C$_6$H$_2$ |
| H | 2-CH$_3$, 4-OCH$_3$—C$_6$H$_3$ |
| H | 2-Cl, 4-OCH$_3$—C$_6$H$_3$ |
| H | 4-OCF$_3$—C$_6$H$_4$ |
| H | 2-OCHF$_2$—C$_6$H$_4$ |
| H | 3-OCHF$_2$—C$_6$H$_4$ |
| H | 4-OCHF$_2$—C$_6$H$_4$ |
| H | 4-(OCF$_2$CHF$_2$)—C$_6$H$_4$ |
| H | 2-F, 4-OCHF$_2$—C$_6$H$_3$ |
| H | 4-(OCH$_2$CH$_3$)—C$_6$H$_4$ |
| H | 4-[OC(CH$_3$)$_3$]—C$_6$H$_4$ |
| H | 3-(CO$_2$CH$_3$)—C$_6$H$_4$ |
| H | 4-(CO$_2$CH$_3$)—C$_6$H$_4$ |
| H | 4-[CO$_2$C(CH$_3$)$_3$]—C$_6$H$_4$ |
| H | 2,3-[O—CH$_2$—O]—C$_6$H$_3$ |
| H | 3,4-[O—CH$_2$—O]—C$_6$H$_3$ |
| H | 3,4-[O—C(CH$_3$)$_2$—O]—C$_6$H$_3$ |
| H | 3,4-[O—CH$_2$CH$_2$—O]—C$_6$H$_3$ |
| H | 2,3-[(CH$_2$)$_4$]—C$_6$H$_3$ |
| H | 3,4-[(CH$_2$)$_4$]—C$_6$H$_3$ |
| H | CH$_3$ |
| H | CH$_2$CH$_3$ |
| H | CH$_2$CH$_2$CH$_3$ |
| H | C(CH$_3$)$_2$ |
| H | CH$_2$CH$_2$CH$_2$CH$_3$ |
| H | CHCH(CH$_3$)$_2$ |
| H | CH(CH$_3$)CH$_2$CH$_3$ |
| H | C(CH$_3$)$_3$ |
| H | Cyclopropyl |
| H | Cyclohexyl |
| H | Pyridin-2-yl |
| H | 5-CF$_3$-pyridin-2-yl |
| H | 3,4-[OCF$_2$O]—C$_6$H$_3$ |
| H | CH$_2$—C$_6$H$_5$ |
| H | Pyrazin-2-yl |
| H | 5-Chloropyridin-2-yl |

The methyl α-phenylbutenoates of the formula I according to the invention are suitable for controlling harmful fungi and animal pests of the insects, arachnids and nematodes class. They can be employed as fungicides and pesticides in crop protection and in the hygiene, stored material protection and veterinary sectors.

The harmful insects include:

from the order of the butterflies (Lepidoptera), for example, Adoxophyes orana, Agrotis ypsilon, Agrotis segetum, Alabama argillacea, Anticarsia gemmatalis, Argyresthia conjugella, Autographa gamma, Cacoecia murinana, Capua reticulana, Choristoneura fumiferana, Chilo partellus, Choristoneura occidentalis, Cirphis unipuncta, Cnaphalocrocis medinails, Crocidolomia binotalis, Cydia pomonella, Dendrolimus pini, Diaphania nitidalis, Diatraea grandiosella, Earias insulana, Elasmopalpus lignosellus, Eupoecilia ambiguella, Feltia subterranea, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera scitella, Lithocolletis blancardella, Lobesia botrana, Loxostege sticticalis, Lymantria dispar, Lymantria monacha, Lyonetia clerkella, Manduca sexta, Malacosoma neustria, Mamestra brassicae, Mocis repanda, Operophthera brumata, Orgyia pseudotsugata, Ostrinia nubilalis, Pandemis heparana, Panolis flammea, Pectinophora gossypiella, Phthorimaea operculella, Phyllocnistis citrella, Pieris brassicae, Plathypena scabra, Platynota stultana, Plutella xylostella, Prays citri, Prays oleae, Prodenia sunia, Prodenia ornithogalli, Pseudoplusia includens, Rhyacionia frustrana, Scrobipalpula absoluta, Sesamia inferens, Sparganothis pilleriana, Spodoptera frugiperda, Spodoptera littoralis, Spodoptera litura, Syllepta derogata, Synanthedon myopaeformis, Thaumatopoea pityocampa, Tortrix viridana, Trichoplusia ni, Tryporyza incertulas, Zeiraphera canadensis, further Galleria mellonella and Sitotroga cerealella, Ephestia cautella, Tineola bisselliella;

from the order of the beetles (Coleoptera), for example, Agriotes lineatus, Agriotes obscurus, Anthonomus grandis, Anthonomus pomorum, Apion vorax, Atomaria linearis, Blastophagus piniperda, Cassida nebulosa, Cerotoma trifurcata, Ceuthorhynchus assimilis, Ceuthorhynchus napi, Chaetocnema tibialis, Conoderus vespertinus, Crioceris asparagi, Dendroctonus refipennis, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lama bilineata, Lama melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllopertha horticola, Phyllophaga sp., Phyllotreta chrysocephala, Phyllotreta nemorum, Phyllotreta striolata, Popillia japonica, Psylliodes napi, Scolytus intricatus, Sitona lineatus, further Bruchus rufimanus, Bruchus pisorum, Bruchus lentis, Sitophilus granaria, Lasioderma serricorne, Oryzaephilus surinamensis, Rhyzopertha dominica, Sitophilus oryzae, Tribolium castaneum, Trogoderma granarium, Zabrotes subfasciatus;

from the order of the dipterous insects (Diptera), for example, Anastrepha ludens, Ceratitis capitata, Contarinia sorghicola, Dacus cucurbitae, Dacus oleae, Dasineura brassicae, Delia coarctata, Delia radicum, Hydrellia griseola, Hylemyia platura, Liriomyza sativae, Liriomyza trifolii, Mayetiola destructor, Orseolia oryzae, Oscinella frit, Pegomya hyoscyami, Phorbia antiqua, Phorbia

*brassicae, Phorbia coarctata, Rhagoletis cerasi, Rhagoletis pomonella, Tipula oleracea, Tipula paludosa,* further *Aedes aegypti, Aedes vexans, Anopheles maculipennis, Chrysomya bezziana, Chrysomya hominivorax, Chrysomya macellaria, Cordylobia anthropophaga, Culex pipiens, Fannia canicularis, Gasterophilus intestinalis, Glossina morsitans, Haematobia irritans, Haplodiplosis equestris, Hypoderma lineata, Lucilia caprina* [sic], *Lucilia cuprina, Lucilia sericata, Musca domestica, Muscina stabulans, Oestrus ovis, Tabanus bovinus, Simulium damnosum;* from the order of the thrips (Thysanoptera), for example, *Franklinleila fusca, Frankliniella occidentalis, Frankliniella tritici, Haplothrips tritici, Scirtothrips citri, Thrips oryzae, Thrips palmi, Thrips tabaci;* from the order of the hymenopterous insects (Hymenoptera), for example, *Athalia rosae, Atta cephalotes, Atta sexdens, Atta texana, Hoplocampa minuta, Hoplocampa testudinea, Iridomyrmes humilis, Iridomyrmex purpureus, Monomorium pharaonis, Solenopsis geminata, Solenopsis invicta, Solenopsis richteri;* from the order of the bed bugs (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus hesperus, Lygus lineolaris, Lygus pratensis, Nezara viridula, Piesma quadrata, Solubea insularis, Thyanta perditor;* from the order of the plant-sucking insects (Homoptera), for example, *Acyrthosiphon onobrychis, Acyrthosiphon pisum, Adelges laricis, Aonidiella aurantii, Aphidula nasturtii, Aphis fabae, Aphis gossypii, Aphis pomi, Aulacorthum solani, Bemisia tabaci, Brachycaudus cardui, Brevicoryne brassicae, Dalbulus maidis, Dreyfusia nordmannianae, Dreyfusia piceae, Dysaphis radicola, Empoasca fabae, Eriosoma lanigerum, Laodelphax striatella, Macrosiphum avenae, Macrosiphum euphorbiae, Macrosiphon rosae, Megoura viciae, Metopolophium dirhodum, Myzus persicae, Myzus cerasi, Nephotettix cincticeps, Nilaparvata lugens, Perkinsleila saccharicida, Phorodon humuli, Planococcus citri, Psylla mali, Psylla piri, Psylla pyricol, Quadraspidiotus perniciosus, Rhopalosiphum maidis, Saissetia oleae, Schizaphis graminum, Selenaspidus articulatus, Sitobion avenae, Sogatella furcifera, Toxoptera citricida, Trialeurodes abutilonea, Trialeurodes vaporariorum, Viteus vitifolii;* from the order of the termites (Isoptera), for example, *Calotermes flavicollis, Leucotermes flavipes, Macrotermes subhyalinus, Odontotermes formosanus, Reticulitermes lucifugus, Termes natalensis;* from the order of the orthopterous insects (Orthoptera), for example, *Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Schistocerca americana, Schistocerca peregrina, Stauronotus maroccanus, Schistocerca gregaria,* further *Acheta domestica, Blatta orientalis, Blattella germanica, Periplaneta americana;* from the order of the Arachnoidea, for example, phytophagous mites such as *Aculops lycopersicae, Aculops pelekassi, Aculus schlechtendali, Brevipalpus phoenicis, Bryobia praetiosa, Eotetranychus carpini, Eutetranychus banksii, Eriophyes sheldoni, Oligonychus pratensis, Panonychus ulmi, Panonychus citri, Phyllocoptruta oleivora, Polyphagotarsonemus latus, Tarsonemus pallidus, Tetranychus cinnabarinus, Tetranychus kanzawai, Tetranchus pacificus, Tetranychus urticae,* ticks such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Rhipicephalus appendiculatus* and *Rhipicephalus evertsi* as well as animal-parasitic mites such as *Dermanyssus gallinae, Psoroptes ovis* and *Sarcoptes scabiei;* from the class of the nematodes, for example, root gall nematodes, eg. *Meloidogyne hapla, Meloidogyne incognita, Meloidogyne javanica,* cyst-forming nematodes, z.B. *Globodera pallida, Globodera rostochiensis, Heterodera avenae, Heterodera glycines, Heterodera schachtii,* migratory endoparasites and semi-endoparasitic nematodes, eg. *Heliocotylenchus multicinctus, Hirschmanniella oryzae, Hoplolaimus spp, Pratylenchus brachyurus, Pratylenchus fallax, Pratylenchus penetrans, Pratylenchus vulnus, Radopholus similis, Rotylenchus reniformis, Scutellonema bradys, Tylenchulus semipenetrans,* stem and leaf eelworms eg. *Anguina tritici, Aphelenchoides besseyi, Ditylenchus angustus, Ditylenchus dipsaci,* virus vectors, eg. *Longidorus spp, Trichodorus christei, Trichodorus viruliferus, Xiphinema index, Xiphinema mediterraneum.*

The active compounds can be applied as such, in the form of their formulations or the application forms prepared therefrom, eg. in the form of directly sprayable solutions, powders, suspensions or dispersions, emulsions, oil dispersions, pastes, dust compositions, scattering compositions or granules, by spraying, atomizing, dusting, scattering or watering. The application forms depend entirely on the intended uses; in each case they should if possible guarantee the finest dispersion of the active compounds according to the invention.

The methyl α-phenylbutenoates of the formula I are in some cases systemically active as fungicides. They can be employed as foliar and soil fungicides against a broad spectrum of phytopathogenic fungi, in particular from the Ascomycetes, Deuteromycetes, Phycomycetes and Basidiomycetes classes.

They are of particular importance for the control of a multiplicity of fungi on various crop plants such as wheat, rye, barley, oats, rice, corn, grass, cotton, soybeans, coffee, sugar cane, grapes, fruit and decorative plants and vegetable plants such as cucumbers, beans and cucurbits, and on the seeds of these plants.

The compounds I are specifically suitable for the control of the following plant diseases:

*Erysiphe graminis* (powdery mildew) in cereals,

*Erysiphe cichoracearum* and *Sphaerotheca fuliginea* on cucurbits,

*Podosphaera leucotricha* on apples,

*Uncinula necator* on vines,

Puceinia species on cereals,

Rhizoctonia species on cotton and grass,

Ustilago species on cereals and sugar cane,

*Venturia inaequalis* (scab) on apples,

Helminthosporium species on cereals,

*Septoria nodorum* on wheat,

*Botrytis cinerea* (gray mold) on strawberries, vines,

*Cercospora arachidicola* on groundnuts,

*Pseudocercosporella herpotrichoides* on wheat, barley,

*Pyricularia oryzae* on rice,

*Phytophthora infestans* on potatoes and tomatoes,
Fusarium and Verticillium species on various plants,
*Plasmopara viticola* on vines,
Alternaria species on vegetables and fruit.

The novel compounds can also be employed in the protection of materials (preservation of wood), eg. against *Paecilomyces variotii*.

They can be converted into the customary formulations, such as solutions, emulsions, suspensions, dusts, powders, pastes or granules. The use forms here depend on the particular intended use; in each case they should if possible guarantee the finest dispersion of the active compounds.

The formulations are prepared in a known manner, eg. by extending the active compound with solvents and/or carriers, if desired using emulsifiers and dispersants, where if water is used as a diluent other organic solvents can also be used as auxiliary solvents.

Suitable auxiliaries for this purpose are mainly:

solvents such as aromatics (eg. xylene), chlorinated aromatics (eg. chlorobenzenes), paraffins (eg. petroleum fractions), alcohols (eg. methanol, butanol), ketones (eg. cyclohexanone), amines (eg. ethanolamine, dimethylformamide) and water;

carriers such as ground natural minerals (eg. kaolins, aluminas, talc, chalk) and ground synthetic minerals (eg. highly disperse silica, silicates);

emulsifiers such as nonionic and anionic emulsifiers (eg. polyoxyethylene fatty alcohol ethers, alkylsulfonates and arylsulfonates) and dispersants such as lignin-sulfite waste liquors and methylcellulose.

Suitable surface-active substances are the alkali metal, alkaline earth metal and ammonium salts of aromatic sulfonic acids, eg. lignosulfonic, phenolsulfonic, naphthalenesulfonic and dibutylnaphthalenesulfonic acid, and also of fatty acids, alkyl- and alkylarylsulfonates, alkyl-, lauryl ether and fatty alcohol sulfates, as well as salts of sulfated hexa-, hepta- and octadecanols, and also of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenol ether, ethoxylated isooctyl-, octal- or nonylphenol, alkylphenol or tributylphenylpolyglycol ether, alkylaryl polyether alcohols, isotridecyl alcohol, fatty alcohol ethylene oxide condensates, ethoxylated castor oil, polyoxyethylene alkyl ethers or polyoxypropylene [sic], lauryl alcohol polyglycol ether acetate, sorbitol esters, lignin-sulfite waste liquors or methylcellulose.

Aqueous use forms can be prepared from emulsion concentrates, dispersions, pastes, wettable powders or water-dispersible granules by addition of water. To prepare emulsions, pastes or oil dispersions, the substrates [sic] can be homogenized in water as such or dissolved in an oil or solvent, by means of wetting agents, adhesives, dispersants or emulsifiers. However, concentrates consisting of active substance, wetting agent, adhesive, dispersant or emulsifier and possibly solvent or oil can also be prepared which are suitable for dilution with water.

Powder, scattering and dusting compositions can be prepared by mixing or joint grinding of the active substances with a solid carrier.

Granules, eg. coated, impregnated and homogeneous granules, can be prepared by binding the active compounds to solid carriers.

Solid carriers are mineral earths such as silica gel, silicic acids, silica gels [sic], silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products, such as cereal flour, tree bark meal, wood meal and nutshell meal, cellulose powder or other solid carriers. The active compound concentrations in the ready-to-use preparations can be varied within relatively wide ranges.

Very generally, the compositions contain from 0.0001 to 95% by weight of active compound.

Formulations containing more than 95% by weight of active compound can be applied highly successfully in the ultra-low volume process (ULV), it even being possible to use the active compound without additives.

For use as fungicides, concentrations of from 0.01 to 95% by weight, preferably of from 0.5 to 90% by weight, of active compound are recommended. For use as insecticides, formulations containing from 0.0001 to 10% by weight, preferably from 0.01 to 1% by weight, of active compound are suitable.

The active compounds are normally employed in a purity of from 90% to 100%, preferably from 95% to 100% (according to NMR spectrum).

Examples of such preparations are:

I. a solution of 90 parts by weight of a compound I according to the invention and 10 parts by weight of N-methyl-α-pyrrolidone, which is suitable for application in the form of very small drops;

II. a solution of 20 parts by weight of a compound I according to the invention in a mixture of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid, 5 parts by weight of the addition product of 40 mol of ethylene oxide to 1 mol of castor oil; a dispersion is obtained by finely dispersing the formulation in water.

III. a solution of 20 parts by weight of a compound I according to the invention in a mixture of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil; a dispersion is obtained by finely dispersing the formulation in water.

IV. an aqueous dispersion of 20 parts by weight of a compound I according to the invention in a mixture of 25 parts by weight of cyclohexanone, 65 parts by weight of a petroleum fraction of boiling point from 210° to 280° C. and 10 parts by weight of the addition product of 40 mol of ethylene oxide to 1 mol of castor oil; a dispersion is obtained by finely dispersing the formulation in water.

V. a mixture, ground in a hamer mill, of 20 parts by weight of a compound I according to the invention, 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel; a spray mixture is obtained by finely dispersing the mixture in water;

VI. an intimate mixture of 3 parts by weight of a compound I according to the invention and 97 parts by weight of finely divided kaolin; this dusting composition contains 3% by weight of active compound;

VII. an intimate mixture of 30 parts by weight of a compound I according to the invention, 92 parts by weight of powdered silica gel and 8 parts by weight of liquid paraffin which has been sprayed onto the surface of this silica gel; this preparation gives the active compound a good adhesion;

VIII. a stable aqueous dispersion of 40 parts by weight of a compound I according to the invention, 10 parts by weight of the sodium salt of a phenolsulfonic acid/urea/formaldehyde condensate, 2 parts by weight of silica gel and 48 parts by weight of water, which can be further diluted;

IX. a stable oily dispersion of 20 parts by weight of a compound I according to the invention, 2 parts by weight of the calcium salt of dodecylbenzenesulfonic acid, 8 parts by weight of fatty alcohol polyglycol ether, 2 parts by weight of the sodium salt of a phenolsulfonic acid/urea/formaldehyde condensate and 68 parts by weight of a paraffinic mineral oil;

X. a mixture, ground in a hammer mill, of 10 parts by weight of a compound I according to the invention, 4 parts by weight of the sodium salt of diisobutylnaphthalene-α-sulfonic acid, 20 parts by weight of the sodium salt of a lignosulfonic acid from a sulfite waste liquor, 38-parts by weight of silica gel and 38 parts by weight of kaolin. By finely dispersing the mixture in 10,000 parts by weight of water, a spray mixture is obtained which contains 0.1% by weight of the active compound.

The compounds I are applied by treating the fungi or the seeds, plants, materials or the soil to be protected from fungal attack with a fungicidally active amount of the active compounds.

They are applied before or after the infection of the materials, plants or seeds by the fungi.

Depending on the type of effect desired, the application rates are from 0.02 to 3 kg of active compound per ha, preferably from 0.1 to 1 kg/ha.

In seed treatment, amounts of active compound of from 0.001 to 50 g, preferably from 0.01 to 10 g, per kilogram of seed are in general needed.

The application rate of active compound for controlling pests under outdoor conditions is from 0.02 to 10, preferably from 0.1 to 2.0 kg/ha.

The compounds I, on their own or in combination with herbicides or fungicides, can also be applied jointly mixed with further crop protection agents, for example with growth regulators or with agents for controlling pests or bacteria. Of interest is also the miscibility with fertilizers or with mineral salt solutions which are employed for eliminating nutritional and trace element deficiencies.

The crop protection agents and fertilizers can be added to the compositions according to the invention in a weight ratio of from 1:10 to 10:1, if appropriate even immediately before use (tank mix). On mixing with fungicides or insecticides, in many cases an increase in the fungicidal spectrum of action is obtained here.

The following list of fungicides with which the compounds according to the invention can be applied together is intended to illustrate the combination possibilities, but not restrict them:

sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediamine bisdithiocarbamate, tetramethylthiuram disulfides [sic], ammonia complex of zinc N,N-ethylenebisdithiocarbamate, ammonia complex of zinc N,N'-propylenebisdithiocarbamate, zinc N,N'-propylenebisdithiocarbamate, N,N'-poly-propylenebis (thiocarbamoyl) disulfide; nitro derivatives, such as dinitro-(1-methylheptyl)phenyl crotonate, 2-sec-butyl-4,6-dinitrophenyl 3,3-dimethylacrylate, 2-sec-butyl-4,6-dinitrophenyl isopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-β-[bis-(dimethylamino)-phosphinyl]-3-phenyl-1,2,4-triazole, 2,3--dicyano-1,4--dithioanthraquinone, 2-thio-1,3-dithiolo-β-[4,5-b]quinoxaline, methyl 1-(butylcarbamoyl)-2-benzimidazolecarbamate, 2-methoxycarbonylaminobenzimidazole, 2-(fur-2-yl) benzimidazole, 2-(thiazol-4-yl)-benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thio-1-oxide [sic], 8-hydroxyquinoline or its copper salt, 2,3-dihydro-5-carboxanilido-6-methyl-1,4-oxathiin, 2,3-dihydro-5-carboxanilido-6-methyl-1,4-oxathiin-4,4-dioxide, 2-methyl-5,6-dihydro-4H-pyran-3-carboxanilide, 2-methyl-furan- 3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis(1-(2,2,2-trichloroethyl))formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tertbutylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-yl-ethyl]-1H-1, 2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3, 3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and also various fungicides, such as dodecylguanidine acetate, 3-[3-(3,5-dimethyl-2-oxycyclohexyl)-2-hydroxyethyl]glutarimide, hexachlorobenzene, DL-methyl-N-(2,6-dimethylphenyl)-N-2-furoyl alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3, 5-dichlorophenyl)-2,4-dioxo-1,3-oxazolidine, 3-[3,5-dichlorophenyl(-5-methyl-5-methoxymethyl]-1,3-oxazolidine-2,4-dione [sic], 3-(3,5-dichlorophenyl)-1-isopropylcarbamoylhydantoin, N-(3,5-dichlorophenyl)-1,2-dimethyl-cyclopropane-1,2-dicarboximide, 2-cyano-[N ethylaminocarbonyl-2-methoximino]-acetamide, 1-[2-(2,4-dichlorophenyl)pentyl]-1H-1,2,4-triazole, 2,4-difluoro-α-

(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole.

SYNTHESIS EXAMPLES

The procedures described in the synthesis examples below were used with appropriate modification of the starting compounds to obtain further compounds I. The compounds thus obtained are listed with physical data in the following table.

Example 1

Methyl α-{2-[1-(4-chlorophenyl)pyrazol-3-yloxymethyl]phenyl}but-2-enoate 1.a Methyl α-(2-bromomethylphenyl)but-2-enoate Hydrogen bromide was passed at –5° C. into a solution of 14.8 g of methyl α-[2-(2-methylphenyloxymethyl)phenyl]but-2-enoate in 250 ml of methylene chloride until it was saturated (about 18 g of HBr). After termination of the reaction (about 2 h at 25° C.), the solvent was distilled off under reduced pressure. The residue thus obtained was taken up in 300 ml of cyclohexane. The solution was washed with 5% strength sodium hydroxide solution and then with water. After drying and concentrating the organic phase, 8 g of the title compound were obtained (m.p.: 64°–66° C.).

1.b 1-(4-Chlorophenyl)-3-hydroxypyrazole

A solution of 57.5 g of 4-chlorophenylhydrazine hydrosulfate in 1,000 ml of tert-butanol was first treated in portions with 100.8 g of potassium tert-butoxide and then (after stirring for 10 min) in the course of 45 min at 45° C.–50° C. with a solution of 27.7 g of methyl propiolate in 90 ml of tertbutanol. After 1 h at boiling point, the mixture was allowed to cool and the solvent was removed under reduced pressure. The residue thus obtained was dissolved in 1,200 ml of water. The aqueous phase was first washed with methylene chloride and then acidified, the product being deposited as a solid. 47.6 g of the title compound were obtained, m.p.: 185°–187° C.

1.c A mixture of 2.43 g of the product from 1.b, 2.58 g of potassium carbonate, 3.36 g of the product from 1.a and 33 ml of dimethylformamide was stirred at 60° C. for 4 h. After cooling, the reaction mixture was taken up in 300 ml of water. The product was isolated from the organic phase after extraction of the aqueous solution with methyl tert-butyl ether and then purified by chromatography. (Silica gel, cyclohexane/MTBE 3:1). (4.5 g of the title compound, m.p.: 65°–66° C.).

Example 2

Methyl α-{2-[1-phenyl-4,5-dihydropyrazol-3-yloxymethyl]phenyl}but-2-enoate

A mixture of 2.43 g of N-phenylpyrazolidin-3-one, 3.1 g of potassium carbonate, 4.04 g of the product from 1.a and 40 ml of dimethylformamide was stirred at 60° C. for 4 h. After cooling, the reaction mixture was taken up in 300 ml of sodium chloride solution (dilute). The product was isolated from the organic phase after extraction of the aqueous solution with methyl tert-butyl ether and then purified by chromatography on silica gel using cyclohexane/methyl tert-butyl ether 5:1 (1.4 g of the title compound, m.p.: 90°–92° C.).

TABLE

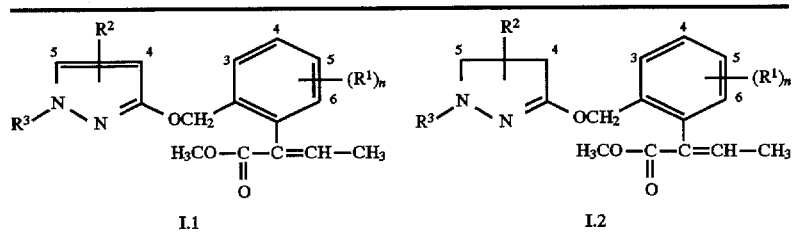

| No. | Formula | $R^1_n$ | $R^2$ | $R^3$ | m.p. [°C.]/IR[cm$^{-1}$]/$^1$H-NMR[ppm] |
|---|---|---|---|---|---|
| 1 | I.1 | H | H | Phenyl | 68–69 |
| 2 | I.1 | H | H | 4-Methylphenyl | 65–66 |
| 3 | I.1 | H | H | 3-Chlorophenyl | 58–59 |
| 4 | I.1 | H | H | 4-Chlorophenyl | 65–66 |
| 5 | I.1 | H | H | 4-Fluorophenyl | 53–54 |
| 6 | I.1 | H | H | 2,4-(Cl)$_2$-phenyl | 72–74 |
| 7 | I.1 | H | H | 2,4-(CH$_3$)$_2$-phenyl | 1716, 1541, 1483, 1463, 1434, 1358, 1253, 1206, 1036, 747 |
| 8 | I.1 | H | H | 2-CH$_3$-4-Cl-phenyl | 1715, 1543, 1495, 1480, 1465, 1357, 1254, 1036, 940, 748 |
| 9 | I.1 | H | H | 2-Cl-phenyl | 1715, 1546, 1495, 1477, 1451, 1358, 1254, 1036, 758 |
| 10 | I.1 | H | H | 3,5-(Cl)$_2$-phenyl | 90–92 |
| 11 | I.1 | H | H | 2,6-(Cl)$_2$-phenyl | 1714, 1547, 1494, 1469, 1439, 1356, 1254, 1037, 793, 749 |
| 12 | I.1 | H | H | 2-CH$_3$-phenyl | 1715, 1541, 1482, 1463, 1435, 1358, 1254, 1048, 1036 |

TABLE-continued

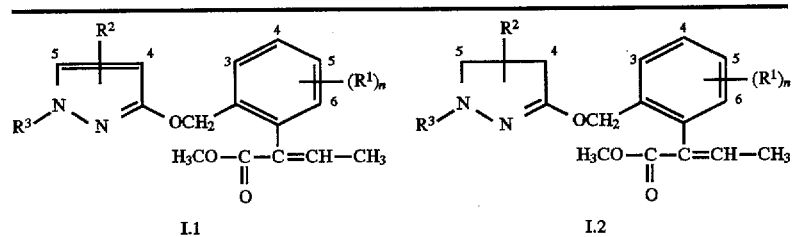

| No. | Formula | $R^1_n$ | $R^2$ | $R^3$ | m.p. [°C.]/IR[cm$^{-1}$]/$^1$H-NMR[ppm] |
|---|---|---|---|---|---|
| 13 | I.1 | H | H | 3-CH$_3$-phenyl | 1715, 1545, 1495, 1483, 1465, 1356, 1253, 1052, 1036 |
| 14 | I.1 | H | H | 4-OCH$_3$-phenyl | 1714, 1543, 1517, 1484, 1465, 1442, 1359, 1251, 1049, 1035 |
| 15 | I.1 | H | H | 2,5-(Cl)$_2$-phenyl | 1715, 1548, 1490, 1472, 1434, 1346, 1254, 1056, 1029, 747 |
| 16 | I.1 | H | H | 3,4-(Cl)$_2$-phenyl | 97–98 |
| 17 | I.1 | H | H | 3-CF$_3$-phenyl | 78–79 |
| 18 | I.1 | H | H | 5-CF$_3$-pyridin-2-yl | 54–56 |
| 19 | I.1 | H | 4-Cl | 4-CH$_3$-phenyl | 67–68 |
| 20 | I.1 | H | 4-Cl | 4-Cl-phenyl | 1713, 1555, 1512, 1496, 1435, 1357, 1255, 1123, 936, 828 |
| 21 | I.1 | H | H | 3-OCH$_3$-phenyl | 1714, 1607, 1597, 1545, 1476, 1356, 1252, 1220, 1046, 1037 |
| 22 | I.1 | H | H | 3,4-[O—CF$_2$—O]—phenyl | 69–71 |
| 23 | I.1 | H | 4-COOCH$_3$ | 4-Cl-phenyl | 118–119 |
| 24 | I.1 | H | 4-COOCH$_3$ | 2,4-(Cl)$_2$-phenyl | 1715, 1564, 1511, 1494, 1436, 1298, 1284, 1254, 1209, 1112 |
| 25 | I.1 | H | H | 4-CF$_3$-phenyl | 1714, 1617, 1551, 1435, 1329, 1323, 1255, 1121, 1112 |
| 26 | I.1 | H | H | Pyridin-2-yl | 1715, 1594, 1547, 1485, 1471, 1451, 1355, 1254, 1047, 776 |
| 27 | I.1 | H | 5-CH$_3$ | Phenyl | 73–74 |
| 28 | I.1 | H | 5-CF$_3$ | 2,4-(Cl)$_2$-phenyl | 1,61 (d,3H); 3,69 (s,3H); 5,08 (s,2H); 6,19 (s,1H); 7,08–7,60 (8H) |
| 29 | I.1 | H | 4-NO$_2$ | 2,4-(Cl)$_2$-phenyl | 116–118 |
| 30 | I.1 | H | 4-Cl | 2,4-(Cl)$_2$-phenyl | 112–114 |
| 31 | I.1 | H | 4-COOCH$_3$ | Phenyl | 117–118 |
| 32 | I.1 | H | 4-Cl | 5-CF$_3$-pyridin-2-yl | 107–109 |
| 33 | I.2 | H | H | Phenyl | 90–92 |
| 34 | I.1 | 3-Cl | H | 2,4-Cl$_2$—C$_6$H$_3$ | 1717, 1546, 1477, 1354, 1261, 1218, 1055 |
| 35 | I.1 | 3-Cl | H | 3,5-Cl$_2$—C$_6$H$_3$ | 1715, 1591, 1578, 1549, 1458, 1436, 1352, 1258 |
| 36 | I.1 | 3-Cl | H | 4-OCH$_3$—C$_6$H$_4$ | 1716, 1542, 1517, 1486, 1357, 1252, 1045, 1029 |
| 37 | I.1 | 3-Cl | H | 5-CF$_3$-pyridin-2-yl | 116–118 |
| 38 | I.2 | H | H | 4-Cl—C$_6$H$_4$ | 1715, 1639, 1598, 1495, 1434, 1415, 1354, 1255 |
| 39 | I.2 | H | H | 2,4-Cl$_2$—C$_6$H$_3$ | 115–116 |
| 40 | I.1 | H | H | CH$_2$C$_6$H$_5$ | 1714, 1537, 1490, 1455, 1434, 1362, 1254, 1049, 1036 |
| 41 | I.1 | H | H | CH$_2$—(4-Cl—C$_6$H$_4$) | 1714, 1537, 1492, 1434, 1362, 1254, 1049, 1036, 1016 |
| 42 | I.1 | H | 5-CO$_2$CH$_3$ | CH$_2$C$_6$H$_5$ | 1720, 1543, 1481, 1455, 1435, 1261, 1207, 1089, 1037 |
| 43 | I.1 | H | H | 5-Cl-pyridin-2-yl | 76–78 |
| 44 | I.1 | H | H | 6-Cl-pyridazin-3-yl | 106–108 |
| 45 | I.1 | H | H | pyrazin-2-yl | 89–91 |
| 46 | I.1 | H | 4-Cl | C$_6$H$_5$ | 1713, 1599, 1555, 1512, 1500, 1357, 1254, 1121 |
| 47 | I.1 | H | 4-Cl | pyrazin-2-yl | 97–99 |
| 48 | I.1 | H | 4-Br | 4-Cl—C$_6$H$_4$ | 88–90 |

TABLE-continued

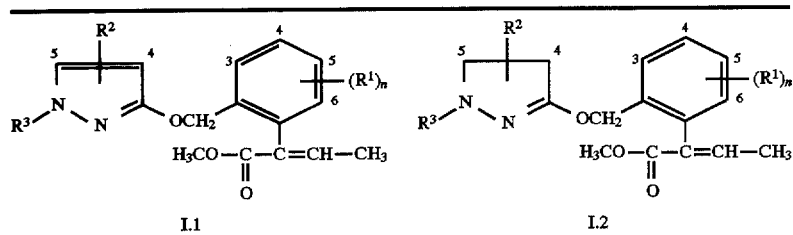

| No. | Formula | $R^1_n$ | $R^2$ | $R^3$ | m.p. [°C.]/IR[cm$^{-1}$]/$^1$H-NMR[ppm] |
|---|---|---|---|---|---|
| 49 | I.1 | H | 4-NO$_2$ | 5-CF$_3$-pyridin-2-yl | 112–114 |
| 50 | I.1 | H | H | CH$_2$—(2,4-Cl$_2$—C$_6$H$_3$) | 61-64 |
| 51 | I.1 | H | H | 2-Cl, 4-F—C$_6$H$_3$ | 1715, 1547, 1505, 1481, 1465, 1358, 1257, 1205, 1051, 1038 |
| 52 | I.1 | H | H | 2-CH$_3$, 4-F—C$_6$H$_3$ | 55–57 |
| 53 | I.2 | H | H | 2-Cl, 4-F—C$_6$H$_3$ | 82–84 |
| 54 | I.1 | H | H | 6-Cl-pyridin-2-yl | 111–113 |

Examples of the Action Against Harmful Fungi

It was possible to show the fungicidal action of the compounds of the formula I by the following experiments:

The active compounds were prepared as a 20% strength emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Emulphor® EL (Emulan® EL, emulsifier based on ethoxylated fatty alcohols) and accordingly diluted to the desired concentration with water.

The comparison compounds used were the following active compounds disclosed in EP-A 513 580:

A Example No. 17 from EP-A 513 580
B Example No. 56 from EP-A 513 580
C Example No. 57 from EP-A 513 580
D Example No. 143 from EP-A 513 580
E Example No. 144 from EP-A 513 580
F Example No. 145 from EP-A 513 580

1. Erysiphe graminis var. tritici

Leaves of wheat seedlings (Frühgold variety) were first treated with the aqueous preparation of the active compounds (16 ppm-containing preparation). After about 24 h, the plants were dusted with spores of wheat mildew (Erysiphe graminis var. tritici). The plants treated in this way were then incubated for 7 days at 20°–22° C. and a relative atmospheric humidity of 75–80%. The extent of the fungal development was then determined. Assessment was carried out visually.

In this test, the plants treated with compounds 1, 2, 3, 4, 5, 6, 10 12, 13, 15, 16 and 17 according to the invention showed an attack of 15% or less, while the plants treated with the known active compounds were attacked to 70% (A and C), 60% (B) or 30% (D, E and F). The attack in the case of the untreated control plants was 70%.

2. Plasmopara viticola

Potted vines (variety: Müller Thurgau) were sprayed with the active compound preparation until dripping wet. After 8 days, the plants were sprayed with a zoospore suspension of the fungus Plasmopara viticola and kept for 5 days at 20°–30° C. at high atmospheric humidity. Before assessment, the plants were then kept for 16 h at high atmospheric humidity.

Assessment was carried out visually.

In this test, the plants treated with 63 ppm-containing preparations of the compounds 1, 2, 4, 5, 6, 7, 8, 9, 12, 13, 14 and 18 according to the invention showed an attack of 5% or less, while the plants treated with 125 ppm-containing preparations of the known active compounds were attacked to 60% (A and F), 40%, (C) or 25% (E). The attack on the untreated control plants was 60%.

We claim:

1. A methyl α-phenylbutenoate of the formula I

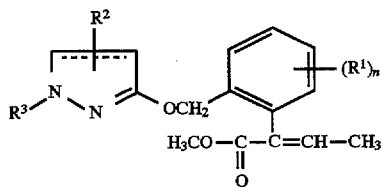

where $=$ is a single or double bond and the index and the substituents have the following meanings:

n is 0, 1, 2, 3 or 4, it being possible for the substituents R$^1$ to be different if n is greater than 1;

R$^1$ is nitro, cyano, halogen, C$_1$–C$_4$-alkyl, C$_1$–C$_4$-haloalkyl or C$_1$–C$_4$-alkoxy;

R$^2$ is hydrogen, nitro, cyano, halogen, C$_1$–C$_4$-alkyl, C$_1$–C$_4$-haloalkyl, C$_1$–C$_4$-alkoxy, C$_1$–C$_4$-alkylthio or C$_1$–C$_4$-alkoxycarbonyl;

R$^3$ is unsubstituted or substituted alkyl, alkenyl or alkynyl;

an unsubstituted or substituted saturated or mono-or diunsaturated ring which, in addition to carbon atoms, optionally contains one to three of the following heteroatoms as ring members: oxygen, sulfur and nitrogen, or an unsubstituted or substituted mono-or binuclear aromatic radical which, in addition to carbon atoms optionally contains one to four nitrogen atoms or one or two nitrogen atoms and an oxygen or sulfur atom or an oxygen or sulfur atom as ring members.

2. A process for preparing the compounds of the formula I as claimed in claim 1, which comprises reacting a benzyl derivative of the formula II

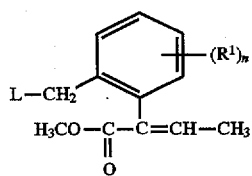

where L is a nucleophilically replaceable group, in the presence of a base with a 3-hydroxy(dihydro)pyrazole of the formula III

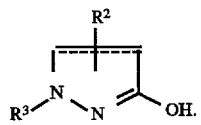

3. A mixture suitable for controlling harmful fungi, containing an inert additive and an active amount of a compound of the formula I as claimed in claim 1.

4. A mixture suitable for controlling animal pests, containing an inert additive and an active amount of a compound of the formula I as claimed in claim 1.

5. A method of controlling harmful fungi, which comprises treating the harmful fungi, their habitat or the plants, surfaces, materials or spaces to be kept free from them with an active amount of a compound of the formula I as claimed in claim 1.

6. A method of controlling animal pests, which comprises treating the pests, their habitat or the plants, surfaces, materials or spaces to be kept free from them with an active amount of a compound of the formula I as claimed in claim 1.

* * * * *